(12) United States Patent
Wong et al.

(10) Patent No.: US 8,606,599 B1
(45) Date of Patent: Dec. 10, 2013

(54) APPARATUS AND METHOD FOR EXECUTING TASKS

(71) Applicant: Medidata Solutions, Inc., New York, NY (US)

(72) Inventors: Isaac Wong, New York, NY (US); Glen de Vries, New York, NY (US); Matthew Szenher, New York, NY (US); Jay Smith, Yardley, PA (US); Andrew Smith, Reading (GB); Joseph Rugilio, Montclair, NJ (US); Bernardo Pontes, Tokyo (JP); Andrew Newbigging, London (GB); Chad Albers, Queens, NY (US)

(73) Assignee: Medidata Solutions, Inc., New York, NY (US)

( * ) Notice: Subject to any disclaimer, the term of this patent is extended or adjusted under 35 U.S.C. 154(b) by 0 days.

(21) Appl. No.: 13/733,572

(22) Filed: Jan. 3, 2013

(51) Int. Cl.
G06Q 50/00 (2012.01)
G06Q 10/00 (2012.01)

(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

2010/0131289 A1* 5/2010 Brandt et al. ..................... 705/2

OTHER PUBLICATIONS

Ferraiolo, Role-Based Access Controls, 2009, CoRR, abs/0903.2171.*

* cited by examiner

Primary Examiner — Tran Nguyen
(74) Attorney, Agent, or Firm — Mayer Brown LLP

(57) ABSTRACT

An apparatus for executing a task includes an authenticator to identify a user, a controller that can receive data from the user, and an authorizer to ensure that the user has access to applications used to execute the task. The controller is able to register or de-register the applications and then determine which if the registered applications should be used to execute the task. The controller then converts the data from the user so that it can be used by the application to execute the task. If the user selects a second task to be executed, the controller can determine which of the registered applications is to be used to execute the second task. Methods for executing multiple tasks are also described.

20 Claims, 10 Drawing Sheets

APPARATUS AND METHOD FOR EXECUTING TASKS

BACKGROUND

People often pursue projects involving data. Businesspeople may have business deals, students may have term projects, engineers may have building projects, and teachers may have courses to plan. Each of these projects may have a life-cycle that includes several stages or phases, such as strategy, planning, execution, and review. Each of these phases may involve different tasks or workflows, and the people performing these tasks may take on different roles within the project. A business deal may involve a project manager, a banker, a lawyer, and an accountant; a term project may involve a planner, a designer, a writer, and a builder; a building project may involve a project manager, a financier, a planner, an engineer, and a technician; and a course plan may involve a main teacher, a teacher's aide, students, and a principal. Individuals may sometimes take on multiple roles within a single project.

People (or entities) pursuing such projects often use computer programs to manage the data. These programs often include a suite of applications, and the people or entities may choose a specific application based on the task or workflow that they want to perform. These suites often do not allow users to easily switch between applications, for example because they request the users to provide credentials every time they access the application. Moreover, sometimes a user wants to view the same data, such as a table, using different applications, such as a word processing application, a spreadsheet application, and a presentation application, but the suite requires the user to open up each application separately, which can be very tedious.

Performing a clinical trial to determine the safety and effectiveness of a pharmaceutical drug or medical device is another example of a project that generates much data and that often uses a suite of computer applications to manage the data. In a clinical trial (called a "clinical study" or "study" in this specification) for a drug, subjects are given doses of the drug and the subject's reaction to the drug is recorded. For a single drug, there may be more than one clinical study, each of which may be carried out with many subjects and at a number of different sites. A clinical study also has a life-cycle made up of phases and involves different people performing various tasks or workflows (or even the same people having multiple roles). The life-cycle of a clinical study may include the design phase, the execution phase, the data collection and analysis phase, and the submission phase. The entities involved may include a sponsor, a principal investigator (PI), contract research organization (CRO), subjects or patients, and regulatory authorities. In many cases, the sponsor is the drug or device manufacturer, such as a pharmaceutical company, but the sponsor may also be an academic medical or research center, a Federal agency such as the National Institutes of Health (NIH) or Departments of Defense or Veterans Affairs, a clinical research center, or a physician or other health care provider. The principal investigator (PI) leads the study and is often a medical doctor, and may also include a research team that comprises doctors, nurses, social workers, and other health care professionals. The clinical study is often administered by the CRO, which may be a person or an organization—commercial, academic, or other—who is contracted by the sponsor to perform one or more of a sponsor's study-related duties and functions. Regulatory authorities, which may include the United States Food and Drug Administration (FDA) and its foreign counterparts, may set the rules by which the clinical studies operate and may be the authorities to whom data are submitted to approve the drug or device.

Each of the users or entities involved with a clinical study may perform many different tasks during the stages of the clinical study. Various software programs have been developed to perform these tasks, but the programs are often usable for only specific stages of a specific study and for a user's specific roles or permitted uses of that software. If a user wants to perform a different task or take on a different role in a study, the user is required to use different programs, often needing to provide credentials when accessing each program. Moreover, sometimes the same data are accessed, viewed, or modified using different programs based on the task to be performed or the role being played, and it is inefficient and somewhat tedious to access individual programs even when operating on the same data.

Figure 1A:
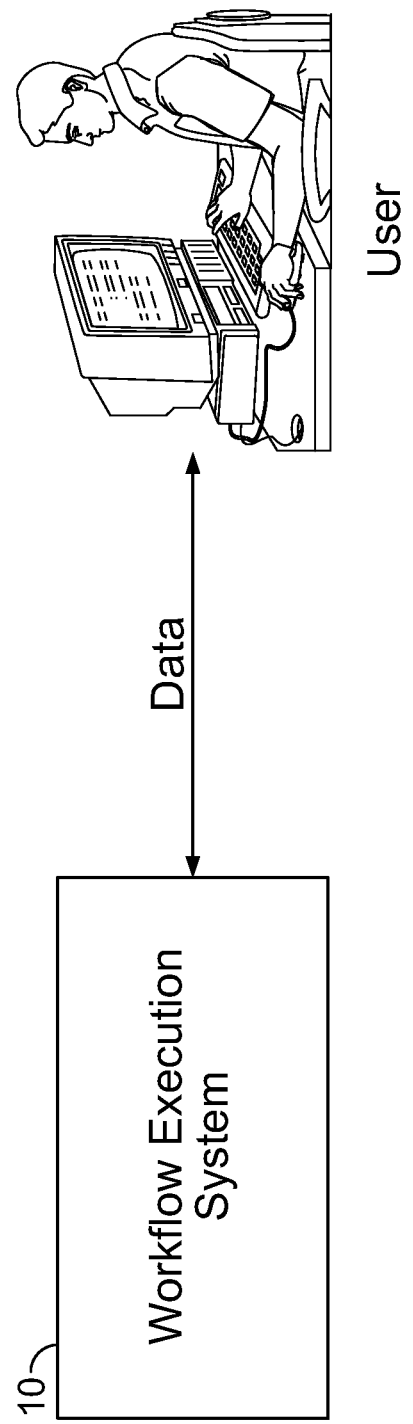
FIG. 1A is a block diagram of a workflow execution system according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Embodiments of the present invention may be used in a variety of applications. Although the present invention is not limited in this respect, the techniques disclosed herein may be used in or with software applications in a variety of fields, clinical drug or device studies, and other projects in which users may desire to view information in a variety of contexts related to the project. Note also that use of the term "data" is not intended to be limiting and may include, but is not limited to, data and/or information.

When performing work on a project that involves data, a user may need to access several programs or applications relating to that project, for example, a business deal. The user may need to open a word processing application to prepare specifications or reports, a spreadsheet application to calculate the financial aspects of the deal, and a presentation application to present the deal to a co-worker or adversary. It would be desirable if the user did not need to "vertically navigate" through each of these applications, that is, initiate or launch a different application every time he or she wanted to perform a different task or workflow. It may also be possible that the same or common data, such as a table, is used by the different applications, requiring the user to open separate applications depending on the context in which the user is working. It may thus also be desirable to be able to "horizontally navigate" among these applications and decouple the data from applications that utilize the data so the system can select the way the data are viewed, modified, or accessed based on the workflow executed by the user.

More specifically, within the context of a project such as a clinical study, a user may have more than one role to play and most likely has more than one workflow to perform, and it would be desirable if the user did not need to vertically navigate through the applications every time he or she wanted to perform a different workflow. Here again, horizontal navigation would be more desirable, especially in situations in which the same (or common) data are being used in the different workflows.

To that end, embodiments of the present invention allow a user to view data in different ways depending on a number of attributes, including but not limited to the role the user is assuming, the workflow the user is performing, and the project or study or site within a study with which the data are used. The system may identify the study, role, and workflow chosen by the user and may select the application best suited for the user to execute the workflow. If the user wants to horizontally navigate to a different study, role, or workflow, the system may adapt to present the data within the specific, appropriate application.

An objective of these embodiments is to provide a platform as a service (PaaS) solution which can decouple data from applications and allow a user to horizontally navigate among tasks rather than vertically navigate among applications.

Reference is now made to FIG. 1A, which is a block diagram of a workflow execution system 10 according to an embodiment of the present invention. As illustrated in FIG. 1A, a user may input data to system 10, which analyzes and processes the data and presents the processed data to the user. A user may be any individual or organization involved in the project, such as a manager, planner, engineer, etc. In the context of a clinical study, a user may include a CRA, a PI, a sponsor, a CRO, or any person or organization that may use workflow execution system 10.

Figure 1B:
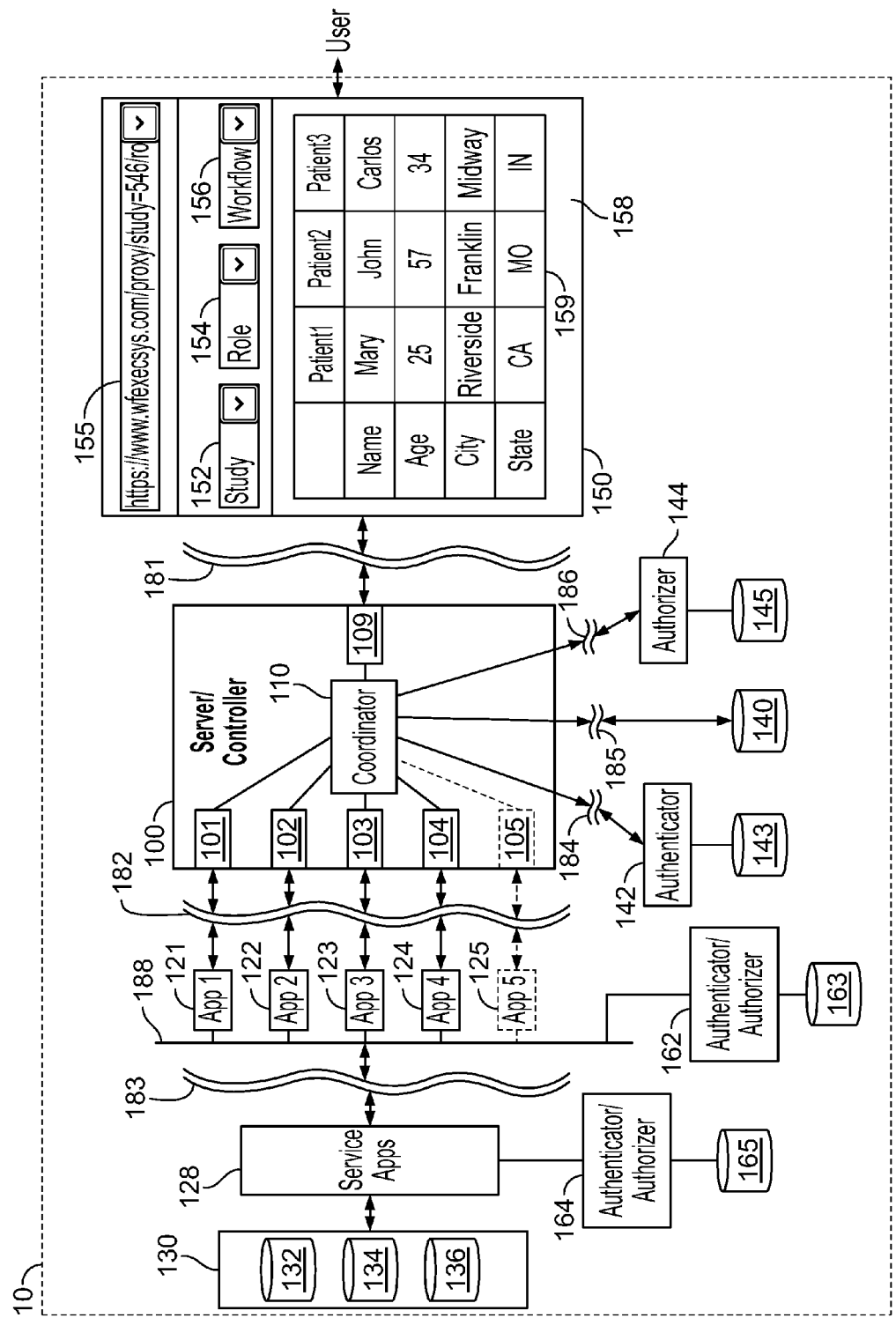
FIG. 1B is a more detailed block diagram of the workflow execution system of FIG. 1A.

FIG. 1B is a more detailed block diagram of the workflow execution system of FIG. 1A. More particularly, workflow execution system 10 may include server/controller 100 and several other parts with which server/controller 100 interacts, including authenticator 142, authorizer 144, database 140, and applications 121, 122, 123, 124 (application 125 will be explained later). Interface 150 is depicted in FIG. 1B as a computer screen and may be part of a computer monitor that displays an Internet or web browser. Interface 150 may also be displayed on a personal digital assistant (PDA) or a handheld cell phone or tablet. On the screen may be drop-down boxes 152, 154, 156 that display, respectively, the project or study at issue, the role of the user, and the task or workflow chosen by the user to perform. Interface 150 may include address box 155, which displays a uniform resource locator (URL) used to access applications 121-124, and information section 158, which may display information, such as table 159, to the user or may include input from the user to be transmitted to server/controller 100. It is desirable for the interface to provide a common user experience (or UX). A user experience comprised of selection tools other than drop-down boxes may accomplish the same purpose and function, such as with radio buttons, hyperlinks, or any other means of receiving a user selection.

Server/controller 100 may communicate with interface 150, applications 121-124, authenticator 142, database 140, and authorizer 144 through connections 181, 182, 184, 185, and 186, respectively. The connections may be any type known to those of skill in the art, including but not limited to wired (for example, a cable) or wireless and may be short (such as within a computer) or distant (such as connecting two computers over the Internet or other network, for example, a WAN (wide area network) or LAN (local area network)).

Server/controller 100 may include an application coordinator 110 that coordinates and processes data transmitted to it from interface 150 and applications 121-124. The data may be communicated via adapters 109 and 101, 102, 103, 104, respectively. These adapters may format the data so that coordinator 110 may process it and so that the outputs of server/controller 100 are properly formatted or rendered for interface 150 and applications 121-124. Coordinator 110 may also interact with authenticator 142 and authorizer 144. Authenticator 142 may take credential information, such as a username and password or biometrics, and compare it to the associations stored in database 143 to determine whether the user is allowed to access the system. Once authenticated, authorizer 144 then retrieves the information associated with the user, such as studies to which the user has access, roles available to the user in those studies, and workflows available to the user to execute in those studies and roles. These associations may be stored in database 145. Authorizer 144 may also later check to make sure the user is associated with a specific study/role/workflow combination that the user selects before server/controller 100 accesses the workflow. It should be noted that such secondary authorization may not always be necessary, for example, if interface 150 and server/controller 100 reside in the same computer.

The general operation of an embodiment of workflow execution system 10 will now be described in the context of a clinical study. Specifically, workflow execution system 10 may exchange data with users in order to display, collect, allow access to, and/or analyze data during the various stages of a clinical study. The data may comprise clinical study data, which may include subject data used to evaluate a drug, such as blood pressure data, heart rate data, and metabolism data. The data may also include monitoring data, such as metadata associated with the collection of subject data, or other data related to the gathering or processing of subject data.

A user may use workflow execution system 10 in the various phases of a clinical trial, such as designing a study, executing a study, collecting and analyzing data, and/or submitting the data to a regulatory agency. Each of these phases may involve several other tasks or workflows. For example, in designing a study, a user, who may be a sponsor or a CRO, may develop a protocol, develop case report forms (CRFs) used to collect the data, develop a data management plan, and select sites. In executing a study a user, who may be a sponsor, a CRO, or a PI, may initiate the sites, obtain informed consent from patients, screen patients, enroll patients, assign patients to an arm of a study, and develop study procedures. In collecting data, a PI may complete CRFs or a sponsor or CRO may perform source data verification, data cleaning, or database locking. In submitting reports to a regulator, a sponsor may collect the CRFs, review queries, perform audits, and prepare other reports. Numerous other tasks or workflows not described herein are likewise included in the present workflow execution system.

In one embodiment of the present invention, three main parts are used to accomplish a task or workflow: server/controller 100, applications 121-124, and interface 150. According to one embodiment, server/controller 100 may identify which applications can perform specific tasks, collect data from the users via interface 150, present the data to the applications, and/or act as a conduit or proxy server between the applications and the user's browser (interface 150), controlling which data and corresponding application are displayed and made accessible to a user, such as through the browser.

Figure 2:
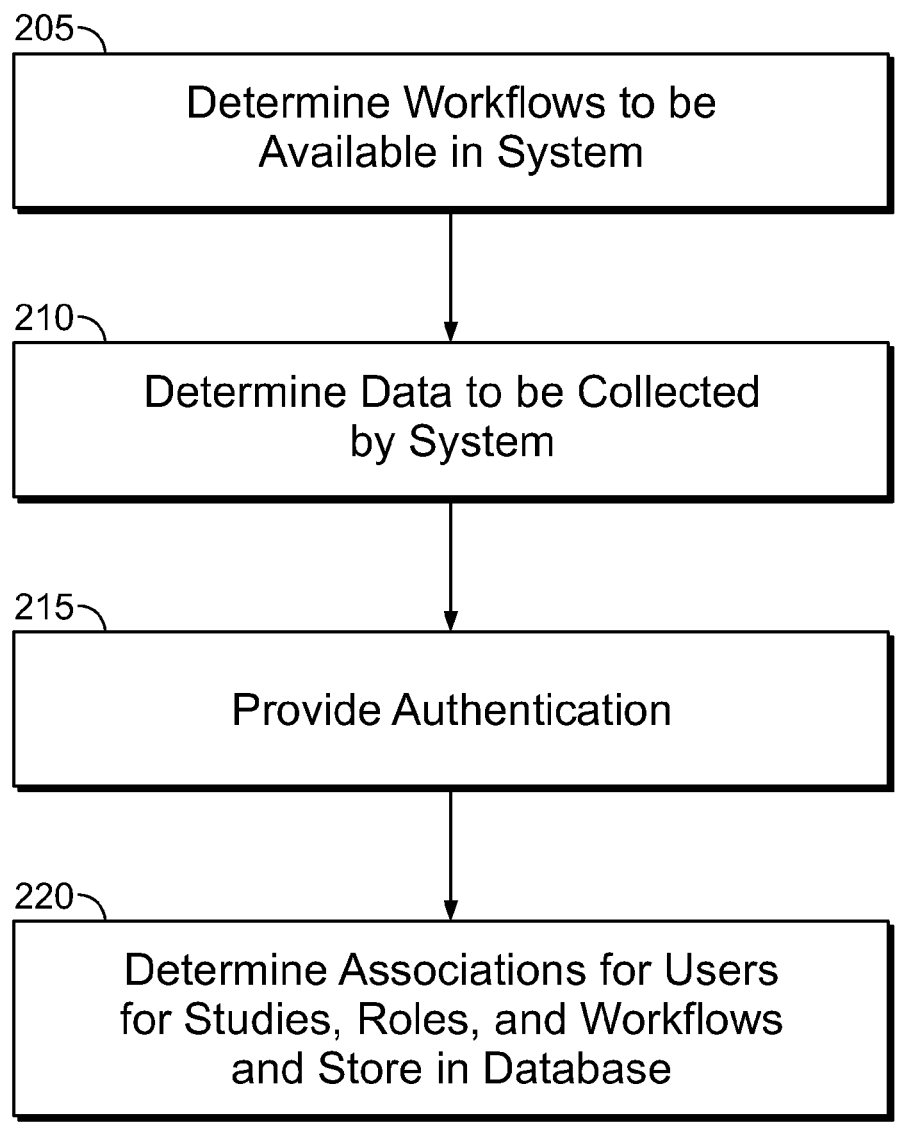
FIG. 2 is a flowchart illustrating how a sponsor may set up a workflow execution system according to an embodiment of the present invention.

FIG. 2 is a flowchart illustrating how a sponsor may set up a workflow execution system according to an embodiment of the present invention. As illustrated in FIG. 2, the sponsor or CRO may set up workflow execution system 10 to address the types of applications and workflows it may need to complete the clinical study. Thus, in operation 205, the sponsor or CRO may determine the workflows that will be available to system users and may choose from among a list of available workflows (for example, to save money or processing time or complexity) or may just have all workflows available for the clinical study. In operation 210, the sponsor or CRO may determine the data to be collected by system 10. In operation 215, the sponsor or CRO may provide authentication for system users by identifying them and providing them credentials (such as a username and password, or possibly biometrics). In operation 220, the sponsor or CRO may associate each user with specific drug studies (clinical studies), specific roles within each study, and specific workflows for each role and study. Alternatively, the sponsor or CRO may select the roles within each study, and those roles may already have associated with them workflows set up by the system. These pre-arranged role-workflow associations may make it easier for a sponsor to register users, since the sponsor does not have to specify each workflow for each user. The credentials and association information may be stored in databases, such as databases 143 and 145, for use in authentication and authorization when a user accesses workflow execution system 10 during the course of a clinical study. Besides the operations shown in FIG. 2, other operations or series of operations may be used to set up a workflow execution system. Moreover, the actual order of the operations in the flowchart may not be critical.

Examples of roles that may be set up in the system include programmers, biostatisticians, clinical research associate (CRA), site monitor, data manager, EDC study builder, patient informed consent specialist, patient recruitment specialist, R&D senior manager, clinical research coordinator (CRC), study coordinator, vendor, CRO manager; clinical quality manager, pharmacovigilance specialist, principal investigator, etc.

In general, workflows associated with a clinical study correspond to study design, study execution, data collection and analysis, and submission of data to regulatory agencies. Study design may include workflows corresponding to protocol development, development of informed consent and case report forms (CRFs), data management planning, site selection, and IRB (ethics) approval. Study execution may include workflows corresponding to investigator meetings, site initiation, and, for each subject, tasks related to informed consent, screening, enrollment, randomization, and performance of study procedures. Data collection and analysis may include workflows corresponding to data collection, CRF completion, source data verification, data cleaning, and database locking. Submission of data to regulatory agencies may include, but is not limited to, workflows corresponding to CRFs, SAS datasets, queries, audit trails, and other reports.

FIGS. 3A-3F illustrate how a user may initiate a session and choose a workflow to be performed with the workflow execution system according to an embodiment of the present invention. Shown in the figures is interface 150 along with drop-down boxes 152, 154, 156 and information section 158. Upon accessing workflow execution system 10, the system may prompt the user in FIG. 3A to provide credentials, such as a username and password, or biometrics, to identify the user to the system (see 309). Once the credentials are provided, coordinator 110 may communicate with authenticator 142 to verify the credentials (which may be stored in database 143).

Figure 3A:
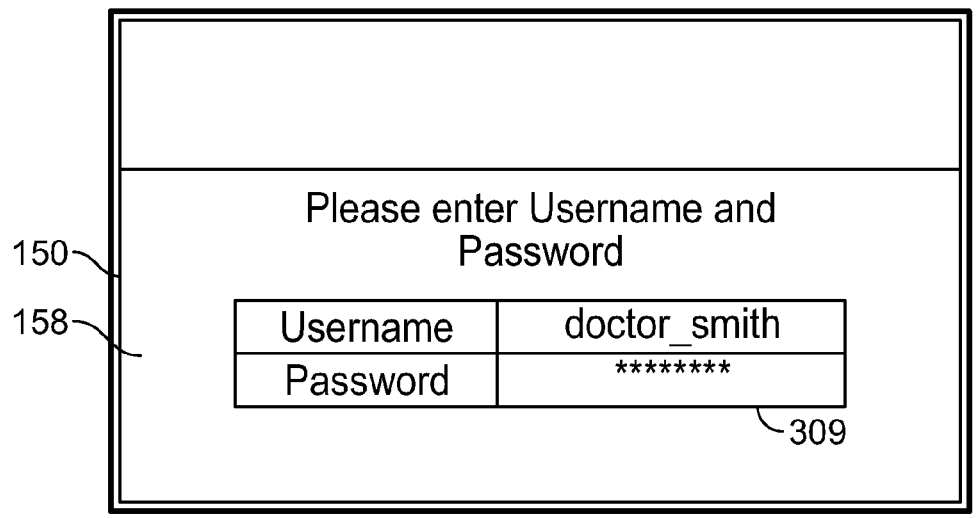
FIGS. 3A-3F illustrate how a user may initiate a session and choose a workflow to be performed using the workflow execution system according to an embodiment of the present invention.
Figure 3B:
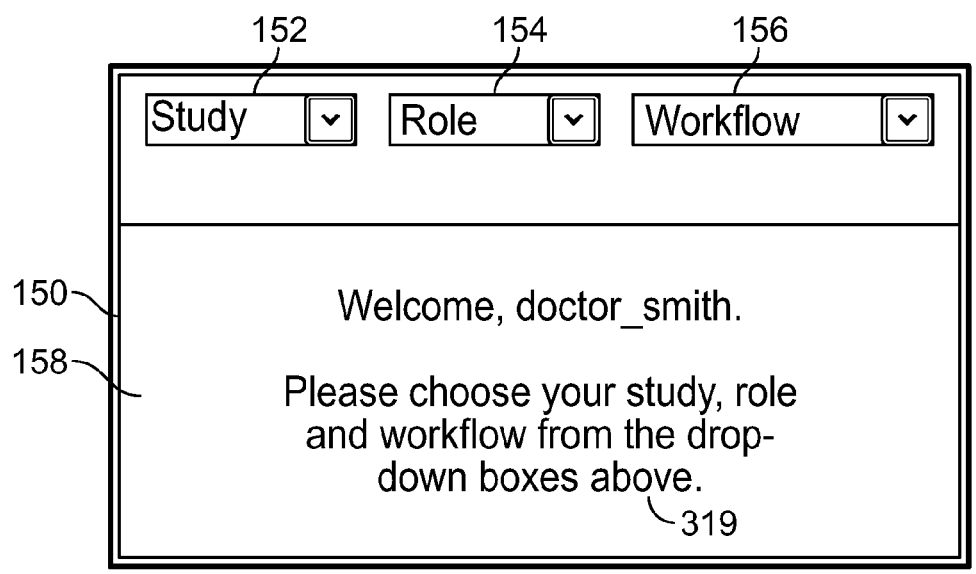
Figure 3C:
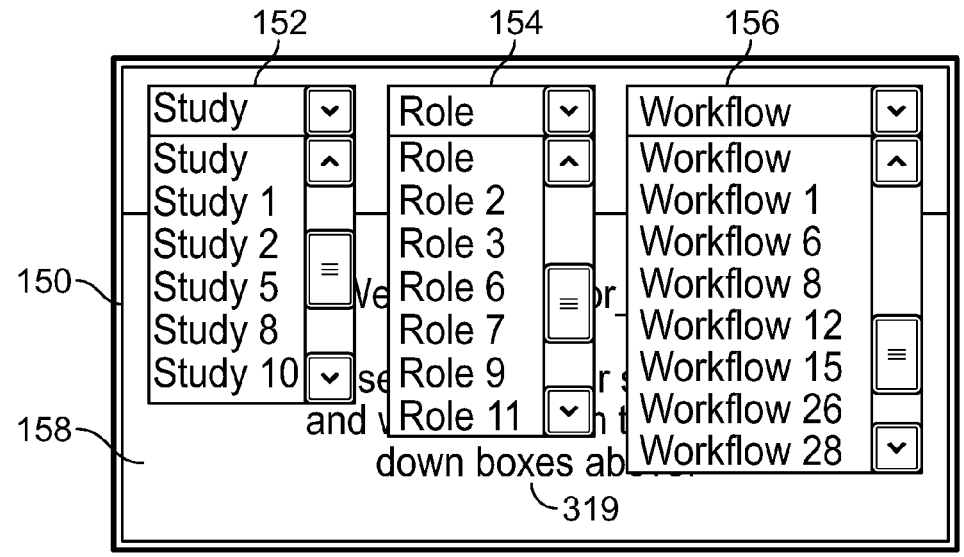

Once verified, the system may retrieve which study/role/workflow combinations are registered to or associated with the user. The retrieval may be accomplished through the execution of software code causing coordinator 110 to communicate with authorizer 144 to retrieve the study/role/workflow combinations which may be stored in database 145, that are registered to the user. FIG. 3B shows dialog 319 prompting the user to choose the study, role, and workflow from the drop-down boxes. FIG. 3C shows all of the studies, roles, and workflows that may be registered to the user. This depiction is for illustration only, since typically only one drop-down box can be activated at one time. As before, a user experience comprised of selection tools other than drop-down boxes may accomplish the same purpose and function, such as with radio buttons, hyperlinks, or any other means of receiving a user selection. Depending on the study chosen, not all the roles shown may be available and, likewise, depending on the role chosen, not all the workflows shown may be available.

Figure 3D:
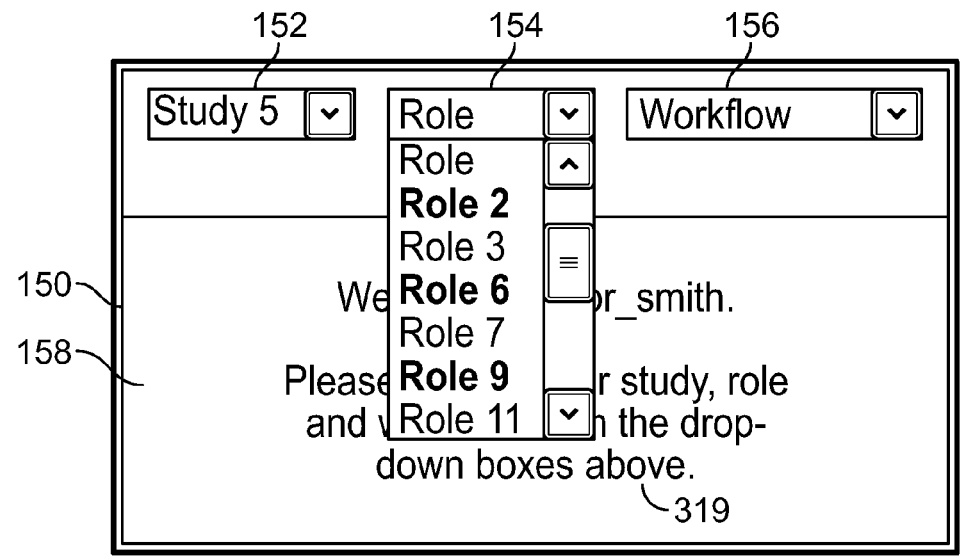
Figure 3E:
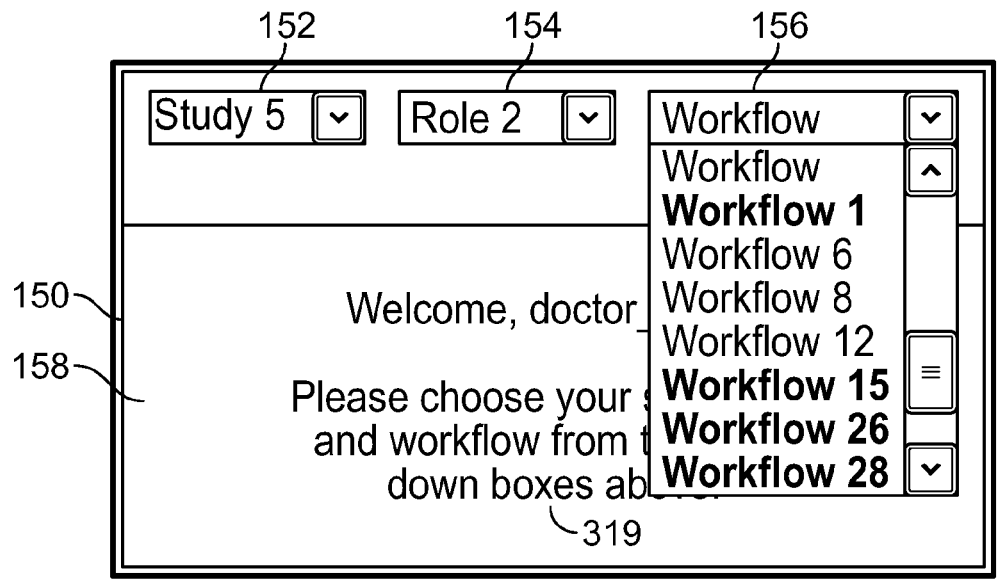
Figure 3F:
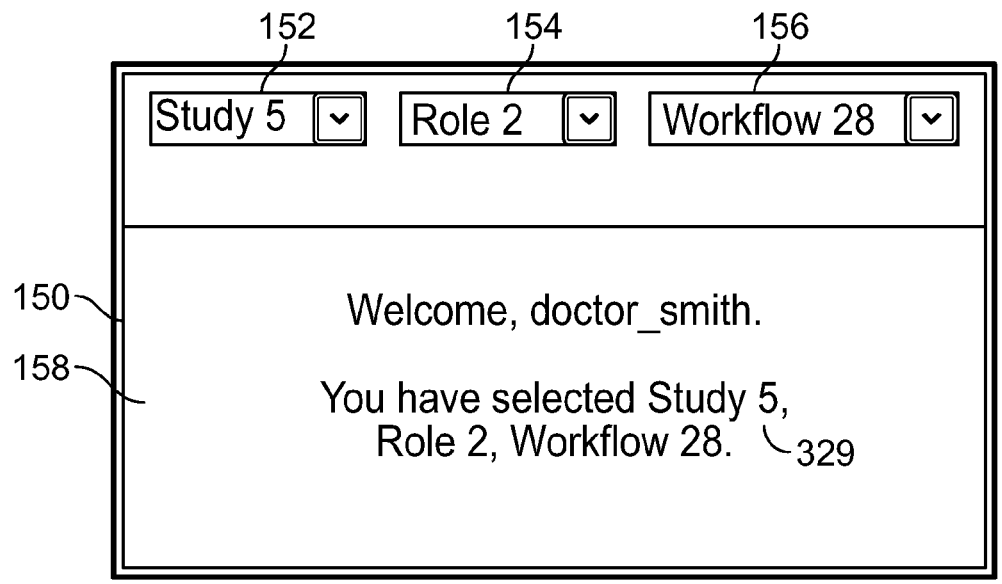

FIGS. 3D-3F show the selection of a possible study/role/workflow combination. FIG. 3D shows that the user selected Study 5. By selecting Study 5, the roles associated with the user for this specific study may be displayed in boldface, and the other roles unassociated with the user for this specific study (but which were shown in FIG. 3C) may be displayed using a different font or grayed out or not displayed at all. One of the associated (i.e., boldfaced) roles may typically be selected by the user, however the user may also select one of the unassociated roles, in which case the user would be able to re-select a different study. (In such a situation, the system may take additional steps to ensure that the re-selection process is proper and that the user is authorized for that re-selection.) FIG. 3E shows that the user selected Role 2. By selecting Role 2, the workflows associated with the user for this specific study and role may be displayed in boldface, and the other workflows unassociated with the user for this specific role and study (but which were shown in FIG. 3C) may be displayed using a different font or grayed out or not displayed at all. One of the associated (i.e., boldfaced) workflows may typically be selected by the user, however the user may also select one of the unassociated workflows, in which case the user would be able to re-select a different role and/or study. (As mentioned above, if a user re-selects a role and/or a study, the system may take additional steps to ensure that the re-selection process is proper and that the user is authorized for that re-selection.) In dialog 329, FIG. 3F shows that the user selected Study 5/Role 2/Workflow 28.

It should be noted that the order of chosen options in FIG. 3 is not intended to be limiting, and one of ordinary skill in the art will realize that the actions can be performed in any appropriate order. For example, in FIG. 3C, the user could first choose from the six available roles, and once that role was chosen, the associated study and workflow choices would then appear in boldface type in those drop-down boxes, and the unassociated study and workflow choices may be displayed in a different font or grayed out or not displayed at all. In that situation, if Role 2 were chosen, then perhaps Studies 1, 5, and 8 would be associated and displayed in boldface. Similarly, if Role 2 were chosen, then before the Study was selected, perhaps Workflows 1, 6, 12, 15, 26, and 28 would be displayed in boldface.

Once the study/role/workflow combination is selected, workflow execution system 10 may begin to execute the workflow. Each workflow may be associated with an application 121-124. These associations may be stored in memory, such as cache memory, within server/controller 100 (not shown in FIG. 1B) or within an external database, such as database 140 and accessed through executable software code (not shown in FIG. 1B). In another embodiment, these associations may be published by the applications using publish-subscribe messaging patterns (also called "pub/sub" patterns), by which each application publishes to the other applications and to server/controller 100 its identity and the studies, roles, and workflows that are associated with it. Such associations may be passed as session variables, allowing server/controller 100 to communicate with applications 121-125 more efficiently via URLs from interface 150, rather than relying on slower cache memory or database memory 140.

Examples of applications 121-124 are software programs associated with clinical studies, such as a protocol design program, a budgeting program, a contract research organization (CRO) program, an electronic data capture (EDC) program, a randomization program, a management program, and a medical coding program. A protocol design program, such as Medidata Solutions' Designer®, may be used to design a clinical study and a study protocol. A budgeting program, such as Medidata Grants Manager®, may be used to determine budgets and allocate resources, investigate sites, manage compliance risks, streamline enrollment, and pay investigators. A CRO program, such as Medidata CRO Contractor®, may be used to help sponsors optimize their relationship with their CROs. An EDC program, such as Medidata Rave®, may be used to electronically capture and manage study data. A randomization program, such as Medidata Balance®, may be used to randomize the study and manage the drug supply for the study. A management program, such as Medidata CTMS™, may be used to manage parts of the clinical study, including site visits and site payments, among other tasks. A medical coding program, such as Medidata Coder®, may be used to set up a centralized coding system. Even though examples of these applications are existing programs, the term "application" is not intended to be limiting and may include a subset of these or similar programs or may be a module of a program or a functional subunit of an application or program.

Each application may also include a number of different workflows. Server/controller 100 may take the workflow selected by the user and may identify the application associated with that workflow. Coordinator 110 may then forward the study and role information to the specified application, possibly using one of the adapters 101-104 to format the request to the application. Server/controller 100 may then act as an intermediary between the selected application and the user to execute the workflow. Server/controller 100 may take the information and/or data transmitted from the application and format or render them for interface 150, possibly using adapter 109. This process may be repeated between the user and the application until the workflow is fully executed or the user otherwise discontinues work on the workflow.

In one embodiment, workflow execution system 10 may include service applications 128 that may perform various common service tasks for applications 121-124, including accessing databases, such as data store 130, which may comprise databases 132, 134, and 136. Applications 121-124 may be connected to service applications 128 via bus 188 and connection 183, which may be an Internet or other network connection (and is the same type of connection as connections 181, 182, 184, 185, 186). The data transmitted between the user and the applications may be stored in data store 130 and may be made available to each of the applications. Alternatively, applications may access data store 130 without using service applications 128, or each application may have its own database (not shown) to store data that only that application will access. Service applications 128 are shown as a single block connected to applications 121-124, but they may also be connected to server/controller 100 and perform service tasks directly for server/controller 100.

In another embodiment, authenticator/authorizers 162, 164 may be associated with applications 121-124 and service applications 128, respectively. These authenticator/authorizers may perform both authentication and authorization, similar to that performed by authenticator 142 and authorizer 144. Authenticator/authorizers 162, 164 may ensure that the request and data from server/controller 100 are genuine, especially because the request and data may have been transmitted over the Internet (e.g., connections 182 and 183). Server/controller 100 may digitally sign its requests using, for example, an authentication program, and authenticator/authorizers 162, 164 may verify the signature, for example using information stored in databases 163, 165. Authenticator/authorizers 162, 164 may also ensure that the user is authorized to perform the specific workflow and that each application is authorized to interact with service applications 128 and data store 130. In general, all transactions from section to section of workflow execution system 10 may be authenticated and/or authorized, but total authentication and authorization may bog the system down, so authentication and authorization may be limited to less trustworthy connections.

One of the benefits of the present invention is that a user may not need to directly access any specific application in order to complete a workflow. The user has to know only what workflow is to be executed and the system may determine which application is best suited to execute the workflow. The system may then format the data to be compatible with the application and may render the resulting data for the user in a manner useful to the user. In some cases, a workflow may be executed using more than one application 121-124, and the system is able to carry out such execution by interacting with each of the needed applications. Without the present invention, the user would need to know which application (or applications) was best suited to execute a specific workflow and specially format a request specific to that application.

Another benefit of the present invention is that the system may be flexible, scalable, and extensible—that is, applications may be added without the knowledge of the user and without complicated rewriting of software. As an example, application 125 may be added to workflow execution system 10, simply by registering the new application with server/controller 100 (and possibly connecting via adapter 105). Registration may involve server/controller 100 recording the workflows that application 125 can execute, as well as the roles that may perform such workflows. Thus, a role, such as a PI, may have dynamically associated with it workflows made possible by the addition of application 125, and all users having the role PI would likewise have access to such additional workflows. Analogously, applications may be removed by de-registering the application from server/controller 100, and the workflows associated with that application would be removed from the various roles.

Another benefit of the present invention is that the applications may be designed to operate in a similar or standard manner, so that their interactions with server/controller 100 are standardized. Part of this standardization may include providing pub/sub messaging patterns discussed above. Such messaging allows workflow execution system 10 to be more flexible and scalable.

The blocks shown in FIGS. 1A and 1B are examples of modules that may comprise workflow execution system 10, and do not limit the blocks or modules that may be part of or connected to or associated with workflow execution system 10. For example, as mentioned before, connections 181, 182, 184, 185, 186 may be short (within a computer) or distant (over a network). Adapters 101-105 are shown within server/controller 100 but may be part of applications 121-125 or may be separate from both the applications and server/controller 100. Similarly, adapter 109 is shown within server/controller 100 but may be part of interface 150 or may be separate from both the interface and server/controller 100. Authenticator 142 and authorizer 144 are shown outside of server/controller 100, but may be within server/controller 100.

Authenticator/authorizers 162, 164 are shown as combined blocks, but they may be separate blocks like authenticator 142 and authorizer 144. The various data stores and databases are shown as separate blocks, but may reside in memory within the blocks with which they are associated. The blocks in FIGS. 1A and 1B may generally be implemented in software or hardware or a combination of the two.

The following embodiments are described in the setting of clinical studies for drugs or medical devices, but it is understood that embodiments of the invention can be used in other fields involving project performance in which data may be presented in different ways to different audiences based on a user's tasks/roles/jobs/functions. For example, a user could take advantage of a system in which various workflows are available on different projects depending on the user's role or roles in those projects. As described earlier, these projects may involve a business deal, a term project, a building project, and a course plan. More generally, a project involving an office suite of applications is contemplated by the present invention.

Figure 4:
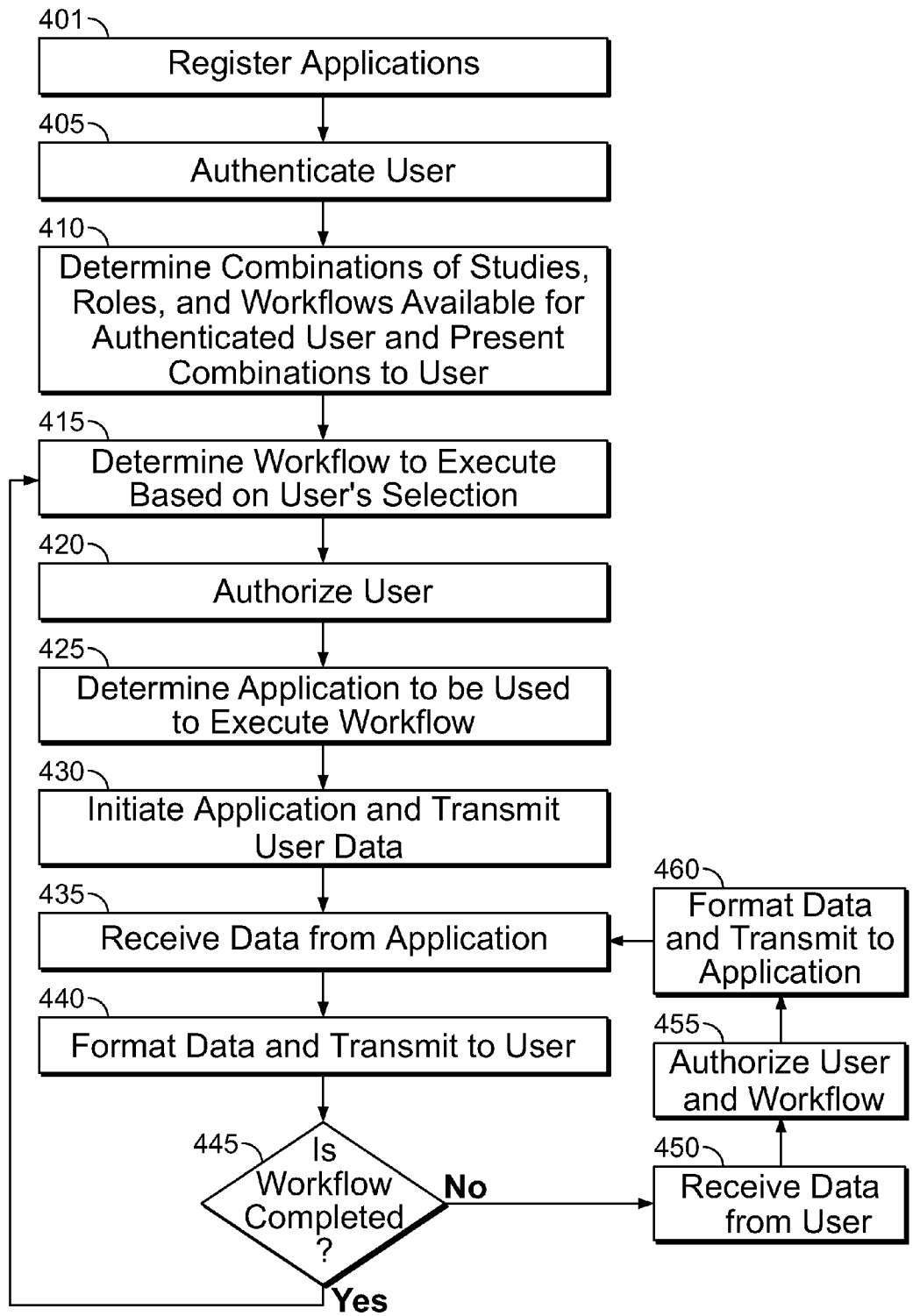
FIG. 4 is a flowchart illustrating the general operation of a workflow execution system according to an embodiment of the present invention.

Reference is now made to FIG. 4, which is a flowchart illustrating the general operation of workflow execution system 10 according to an embodiment of the present invention. In operation 401, server/controller 100 may register one or more of applications 121-125. This may be dynamic, as described above, and may involve recording the workflows that the applications can execute, as well as the roles that may perform such workflows. In operation 405, server/controller 100 may authenticate the user, such as by requesting credentials (e.g., username and password, or biometrics) (see FIG. 3A). In operation 410, server/controller 100 may determine the combinations of studies, roles, and workflows available for the authenticated user and present those combinations to the user. In operation 415, server/controller 100 may determine the workflow to be executed based on the user's selection, as was described above with respect to FIGS. 3B-3F. In operation 420, server/controller 100 may authorize the user to ensure the study/role/workflow combination selected by the user is associated with that user. This operation may not be used if interface 150 and server/controller 100 are within the same computer (e.g., if connection 181 is short), but if connection 181 is distant, such authentication may be desired to ensure that the information from the user was properly communicated to server/controller 100. In operation 425, server/controller 100 may determine which application (e.g., 121-125) is to be used to execute the selected workflow. This may be done by accessing database 140 to retrieve the association between the selected workflow and the application or by reviewing the applications' pub/sub messaging patterns as described above. Such association may include a file path or an address or URL (uniform resource locator) if the application is not located within the same computer as server/controller 100. A URL as contemplated herein may include a raw URL, which may be an address of an object or data, and a platform URL, which is an abstracted raw URL that may describe the data to be acted upon and the desired action or task to be performed on that data. An example of a platform URL may include "design report," because that is the desired action. Determining which application is to be used to execute the selected workflow may include converting a platform URL to a raw URL. In operation 430, server/controller 100 may initiate the application (or call the application) via its path, address, or URL and transmit the user's data to the application as part of the URL. Such information may include the study/role/workflow combination such that the application can properly initiate the workflow.

The selected application may begin executing the workflow and, in operation 435, server/controller 100 may receive data from the application. Server/controller 100 may then format the data and transmit it to the user in operation 440. If this is the end of the workflow (which is determined in operation 445), server/controller 100 returns to operation 415 to await selection of another workflow by the user. If this is not the end of the workflow (determined in operation 445), a loop begins in which data are then received from the user in operation 450. Because interface 150 and server/controller 100 may interact over a network, server/controller 100 may need to authorize the user and the selected workflow again in operation 455. After that, server/controller 100 may format the data from the user and transmit it to the application for processing in operation 460. The loop continues with operations 435, 440, and 445 as described above for server/controller 100 to receive data from the application, format the data and transmit it to the user and then determine whether the workflow is completed. Besides the operations shown in FIG. 4, other operations or series of operations may be used to execute workflows. Moreover, the actual order of the operations in the flowchart may not be critical.

Figure 5:
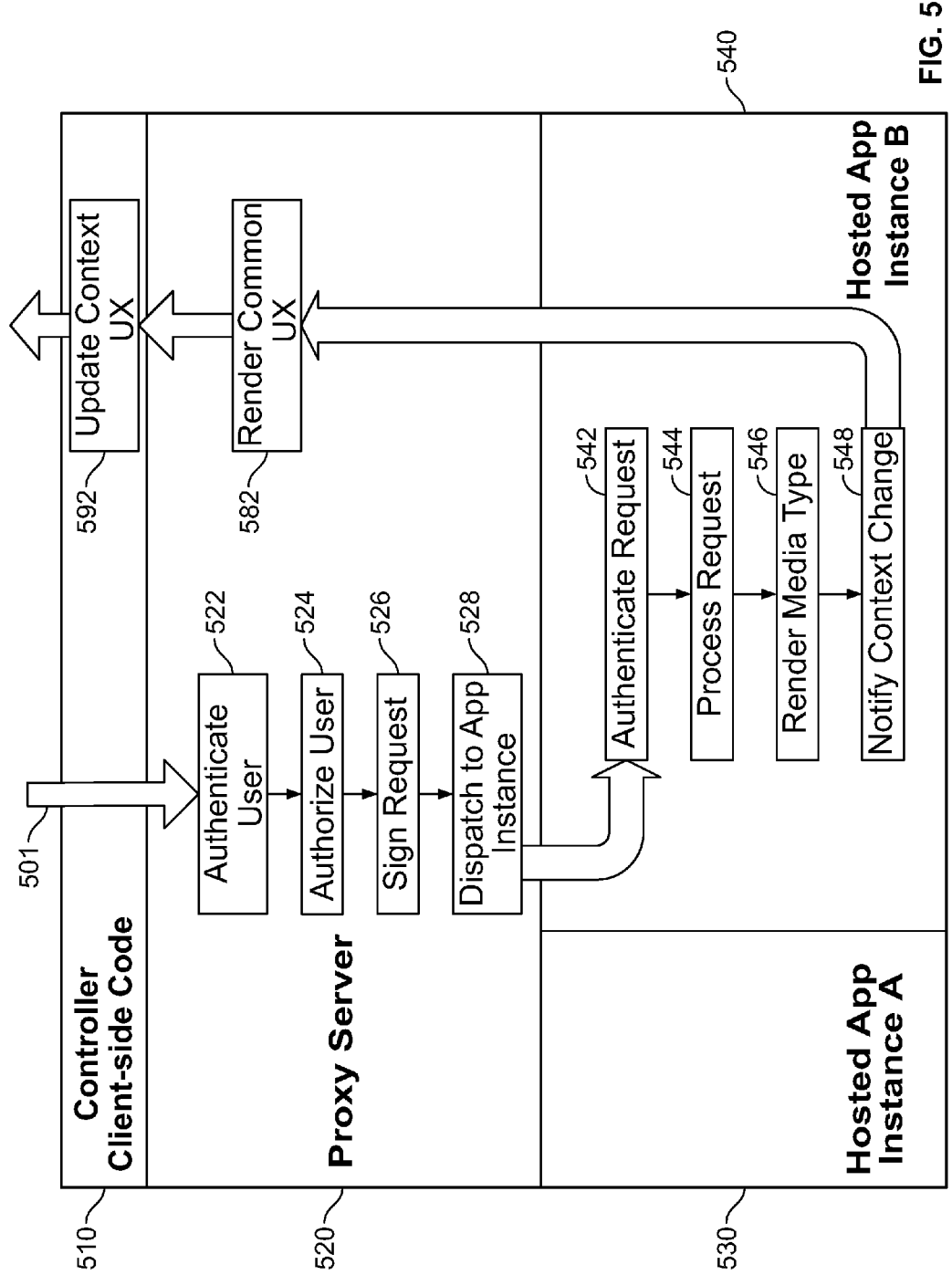
FIG. 5 is a schematic of a hosted proxy architecture of a workflow execution system according to an embodiment of the present invention.

FIG. 5 shows another way of viewing the operation of workflow execution system 10. FIG. 5 is a schematic of a hosted proxy architecture according to an embodiment of the present invention. This architecture includes controller client-side code 510, proxy server 520, hosted application instance A 530, and hosted application instance B 540. A request 501 comes in from the user's web browser and server/controller 100 acts as proxy server 520 for the request. This request may be transmitted as a URL to server/controller 100. The URL may contain the study, role, and workflow selected by the user. Proxy server 520 may authenticate the user in operation 522 by checking the user's sign-in credentials and then authorize the user for the specific study, role, and workflow in operation 524. Proxy server 520 may then begin to forward the request to the application indicated by the chosen workflow. In operation 526, proxy server 520 may digitally sign the request, so that the application can determine that the request is coming from proxy server 520. Then in operation 528, proxy server 528 may dispatch the request to an instance of the hosted application, in this case, hosted application instance B 540. Although only two application instances are shown in FIG. 5, workflow execution system 10 may have a number of instances of each hosted application 121-125 running.

In operation 542, hosted application instance B 540 authenticates the request from proxy server 520, for example by using authenticator 160, and checks the digital signature to ensure it came from proxy server 520. In operation 544, hosted application instance B 540 processes the request from the user, then, in operation 546, hosted application instance B 540 renders its response using some media type, such as HTML, XML, JSON, etc. In operation 548, hosted application instance B 540 may provide (in HTML) a notice of context (or location) change, which includes metadata that identifies the user's study, role, and workflow, and then returns the request to proxy server 520.

In operation 582, proxy server 520 renders (or formats) the request for the common user experience (UX) and then transmits the response to controller client-side code to update the context user experience in operation 592. This may result in information screen 158 of the user's web browser being updated as well as the user's context (e.g., study, role, and workflow), if that also changed.

As discussed above, one advantage of the present invention may be the ability to open multiple instances of applications so as to allow for horizontal navigation, rather than vertical navigation. Vertical navigation requires a user to open a new application to perform a different task. For example, a user may open an email using an email program, but then may need to open a word processing program to view an attachment. In contrast, using horizontal navigation, the user may view the email in the main program and then view the attachment in the same program by opening an instance of the word processing application. This instance may then track and retain the user's context or location.

Figure 6:
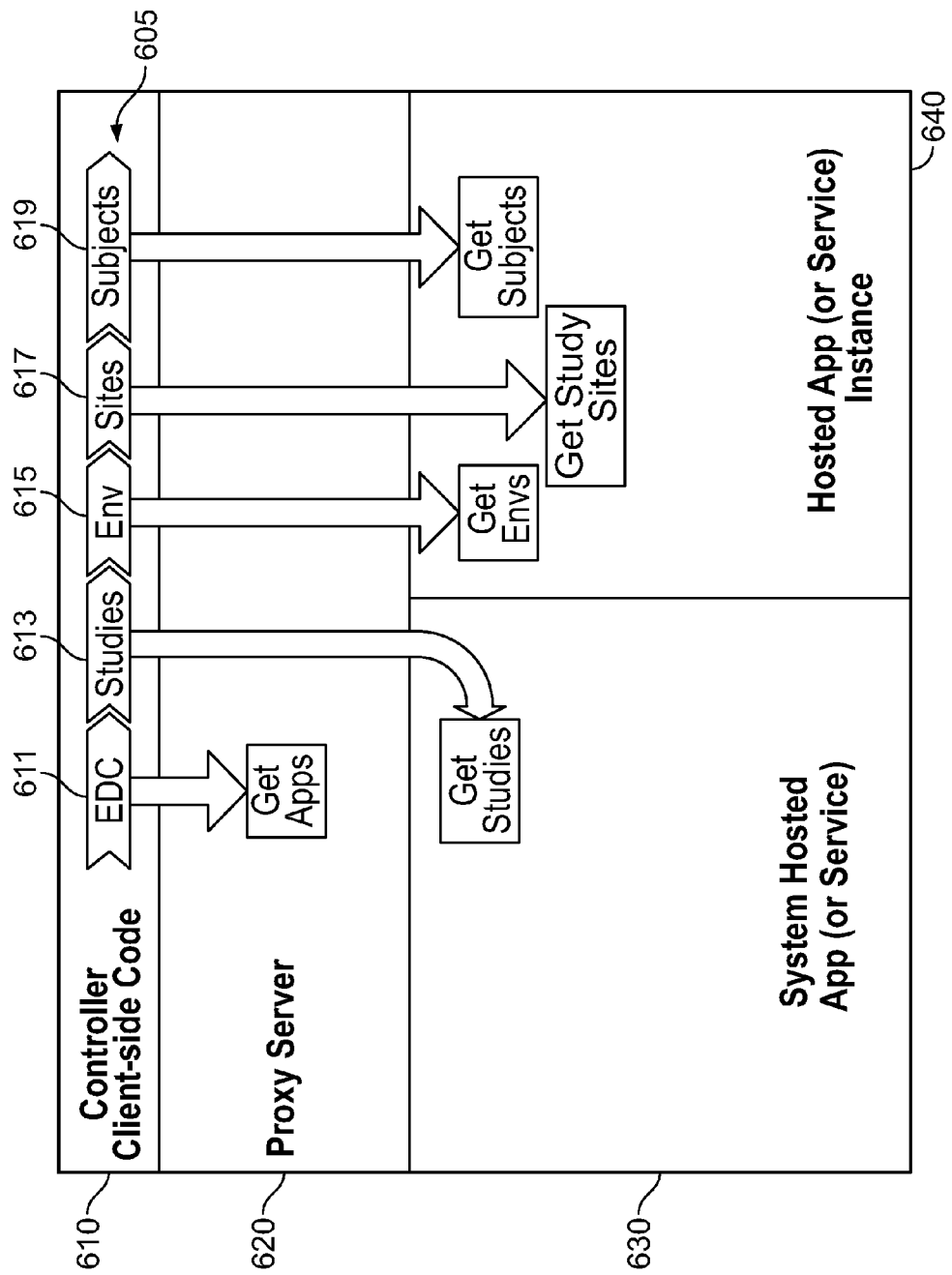
FIG. 6 is a schematic of a context architecture of a workflow execution system according to an embodiment of the present invention.

FIG. 6 shows another way of viewing the operation of workflow execution system 10. FIG. 6 is a schematic of a context architecture according to an embodiment of the present invention. This architecture includes controller client-side code 610, proxy server 620, system hosted application (or service) instance 630, and hosted application (or service) instance 640.

The task shown in FIG. 6 is to fill in context 605, e.g., the current application, study, environment, site, and subject, in controller client-side code 610, which may be rendered on interface 150. To fill in application 611, controller client-side code 610 makes a request for the application from proxy server 620. Application 611 is shown in FIG. 6 as EDC or the electronic data capture application. To fill in study 613, controller client-side code 610 makes a request to system hosted application 630, and the selected study may be rendered through an application programming interface (API). Also, because the connection to this system hosted application 630 may be over the Internet, the request may need to be authenticated to ensure that the user has the proper access to the studies. To fill in environment 615, site 617, and subject 619, controller client-side code 610 makes a request to hosted application instance 640, which in this case is the EDC application, for that information. These may also need authentication, but it is less likely, since the information is generally within a single application instance.

Within this framework, a way of interacting with data is provided whereby data is no longer tied to a specific application from the point of view of the user. A table containing information about patients no longer needs to be viewed in the specific application (such as a spreadsheet) in which the data were entered, for example during patient enrollment. Instead, the same table data could be presented to the user based on the workflow being executed—patient enrollment, data collection, and data analysis, for example—and the user would not need to open up different applications to view the table or data but would only need to specify the workflow being executed and the system would render the information for the user in different ways depending on the workflow.

Figure 7A:
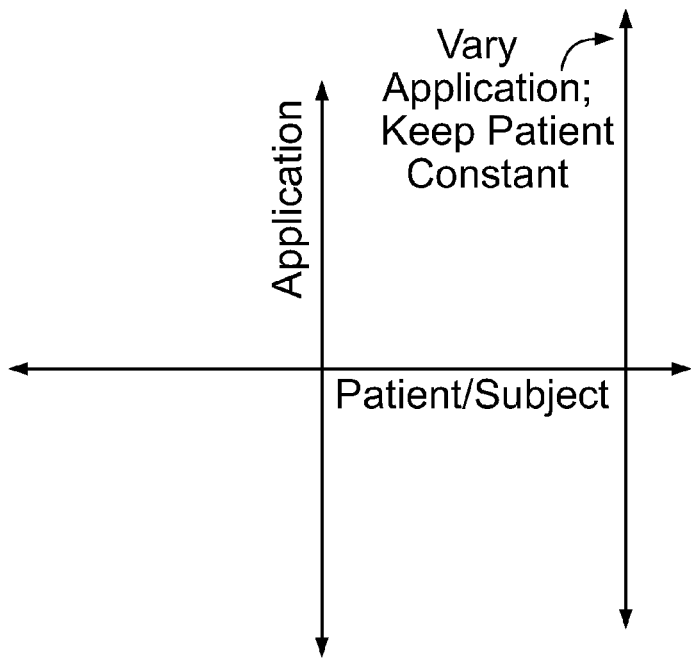
FIGS. 7A-7B are illustrations of some advantages of some embodiments of the present invention.
Figure 7B:
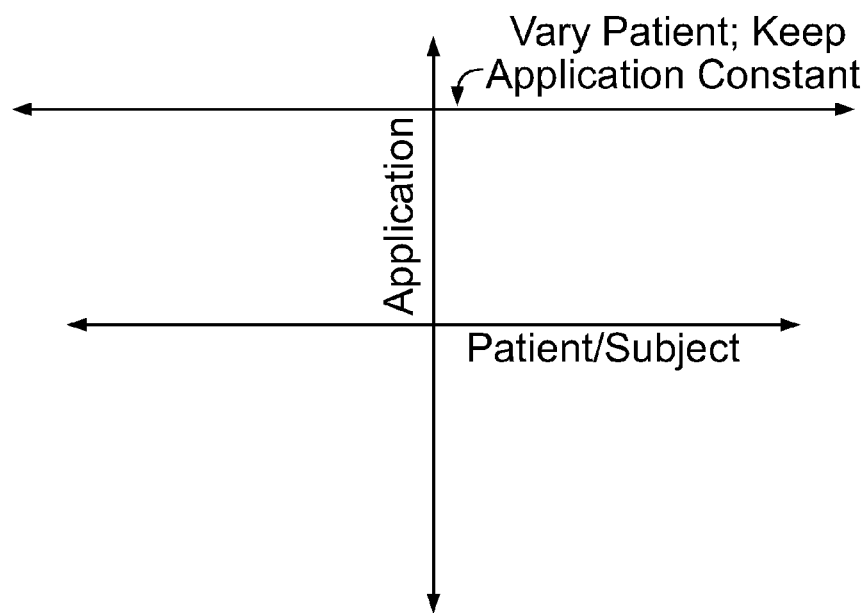

FIGS. 7A and 7B show ways of viewing this aspect of the invention. These figures show graphs of application vs. patients (or subjects). In FIG. 7A, the patient is constant, but the application varies. Before the present invention, a user would need to open different applications to perform different workflows even though the information, underlying subject matter, or task remained the same. With this invention, the user merely needs to specify a different workflow, but the user is still using the same software program. The system identifies the correct application to access and renders the patient's data to the user using interface 150. In FIG. 7B, the application is kept constant, but the patient varies. This may happen if a user is involved in a study and wants to perform the same workflow on multiple patients. Before the present invention, a user would need to open different files within the same application because each patient's data would be kept separate. With this invention, the user merely needs to specify a different patient and then can see how the data vary among the patients, but the user is still using the same software program. The system identifies the correct patient data to access and renders the data to the user using interface 150.

The following are some examples of how the embodiments of the present invention can be used. A user may want to design a case report form (CRF) and then validate its use. Conventionally, this would involve opening up two applications—the form design application (such as Medidata Architect) to design the form and an electronic data capture (EDC) application (such as Medidata Rave®) to validate. But both applications use substantially the same data (or at least have some data in common), that is, the form and its information. With the present invention, the user would use only one software program. The user would be associated with two roles (and at least two workflows)—as a form designer and as a clinical research coordinator (CRC, which may oversee data entry). After specifying the designer role in drop-down box 154 (FIG. 1B) and the design workflow in drop-down box 156, the system would prompt the user to design the form. Then, in order to validate the form, the user would choose the CRC role in drop-down box 154 and the data entry workflow in drop-down box 156 and would then be presented with the form to enter data to ensure that the form works. In addition, if the user was involved in more than one study, then the user could design the form for one study, then choose a different study from drop-down box 152 and be presented with the form for that study. Conventionally, the user would have had to switch files in order to access a form from a different study.

Another example is performing two tasks of collecting data and making a payment to a site. Conventionally, this would involve vertically navigating to two applications—the data collection or EDC application such as Medidata Rave® to collect the data and a clinical trial or study management application such as Medidata CTMS™ to make the payment. But both applications use substantially the same data (or at least have some data in common), that is, the data collected and the fact that the data have been collected. With the present invention, the user would only use one software program, but horizontally navigate from the data collection workflow to the site payment workflow.

Another example involves the multiple workflows that can be performed regarding a shipment of drugs going to a study. One workflow may be performed by the shipper, who assembles the shipment. A second workflow may be performed at the study site, which allows the user to mark the shipment as received or lost. Another example involves the multiple workflows that can be performed regarding the same subject or patient. One workflow may be performed by a clinician to randomize the assignment of the subject in the study. A second workflow may be performed by the subject or patient herself, where she may be entering actual clinical study data on her mobile device. In both of these examples, multiple workflows can be performed using the same or common data, but which previously required two or more different applications to perform them.

In an example of a use of the invention outside of the clinical study environment, a user may receive an email with an attached document. Conventionally, this user would only be able to view the email in an email application and then would need to switch to a word processing application to view the attachment. But using the invention, the user would be able to change the task (e.g., from "view mail" to "view document") and view the email or the document as desired.

The present invention may provide the following benefits, among others. First, it may allow users to horizontally navigate between tasks or workflows, where server/controller 100 remembers the user's context, and the same or common data can be used to perform different tasks. The user is unaware of which underlying applications may be accessed to perform the tasks. Moreover, all the tasks have a common user interface or user experience, thus adding to the perception that a single computer program is being accessed. This contrasts with vertical navigation in which applications had to be started and ended by the user, often requiring the user to provide credentials every time a different application was accessed. Second, the invention may bring unified security to all the hosted applications. It may do this by identifying a fixed set of roles as described earlier. If the role is "principal investigator," then that user will be granted access to all applications needed to carry out that role, and anybody with that role in a specific study will get the same permissions or authorizations. Previously, the user would have to access each application, and each application would then need to grant each user the proper security credentials. Third, the invention may allow users to access data across multiple patients and multiple studies, whereas previously a user would have had to open separate applications (or separate instances of applications) for different patients or different studies and then close them before going on to the next patient or study.

This invention may be implemented as a platform service, detached from individual products or programs and may be implemented over the Internet as a cloud-based service. In the clinical study context, this means that the platform service can perform all tasks needed to complete a clinical study, whereas previously five or more applications would have had to be accessed for such a study. This platform has capabilities—for example, safety, design, randomization, data collection, and study management—not just separate applications that may perform parts of these capabilities.

In sum, apparatuses and methods are described that may be used to execute tasks or workflows. The server/controller acts as an intermediary between an interface and an application or applications. The server/controller determines which application is to be used to execute the workflow and converts the data from the interface into a form compatible with the chosen application. Applications may be added and removed dynamically by registering with the server/controller and having the workflows executed by the applications identified along with the roles that can access those workflows. Data is decoupled from the applications so that multiple workflows can operate on the same or common data without having the user enter and exit specific applications. Such horizontal navigation may be secured by using authenticators when the user changes contexts. The invention allows for task-based rather than application-based execution. Roles are defined with specific permissions and workflows so that a user does not have to know the details about which application performs which workflow.

Note that although the methods and apparatuses described herein have been described with respect to clinical studies for drugs, they are applicable to clinical studies for other items such as medical devices, vaccines, and biologics. They are also applicable to systems other than those involving clinical studies that are capable of having different tasks executed without having the user vertically navigate among different applications.

Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. An apparatus for providing a user access to clinical tasks, comprising:
   a processor;
   a controller component executed by the processor and operative to register a plurality of clinical applications and to receive data from the user, the data including data regarding a first clinical task to be executed for the user; and
   an authenticator component executed by the processor and operative to identify the user;
   wherein the processor is programmed to:

retrieve first records associating users and their identifying information;
determine, using the authenticator component based on the retrieved first records, that the user is identified;
retrieve second records associating clinical tasks and registered clinical applications;
further determine, using the controller component based on the retrieved second records and the first clinical task, a first registered clinical application from the plurality of clinical applications and associated with the first clinical task;
further determine that the first registered clinical application is accessible by the user; and
execute the first clinical task using the first registered clinical application.

2. The apparatus of claim 1, wherein the data received from the user includes a second clinical task to be executed for the user.

3. The apparatus of claim 2, wherein the controller component is further operative to receive data operated on by the first registered clinical application.

4. The apparatus of claim 3, wherein the processor is programmed to:
further determine, using the controller component based on the second clinical task, a second registered clinical application associated with the second clinical task; and
execute the second clinical task using the second registered clinical application and the received data operated on by the first registered clinical application.

5. The apparatus of claim 4, wherein the processor is programmed to further determine that the second registered clinical application is accessible by the user.

6. The apparatus of claim 2, wherein the first clinical task is related to a first clinical study subject and the second clinical task is related to a second clinical study subject.

7. An apparatus for providing a user access to clinical tasks, comprising:
a processor;
a controller component executed by the processor and operative to register a plurality of clinical applications and to receive data from the user, the data including data regarding a first clinical task and a clinical study and a role associated with the first clinical task to be executed for the user; and
an authenticator component executed by the processor and operative to identify the user;
wherein the processor is programmed to:
retrieve first records associating users and their identifying information;
determine, using the authenticator component based on the retrieved first records, that the user is identified;
retrieve second records associating clinical tasks and registered clinical applications;
retrieve third records associating with the users clinical studies and roles within the clinical studies;
further determine, using the controller component based on the retrieved second records, retrieved third records, and the first clinical task, a first registered clinical application from the plurality of clinical applications and associated with the first clinical task; and
execute the first clinical task using the first registered clinical application.

8. The apparatus of claim 7, wherein the processor is programmed to further determine that the first registered clinical application is accessible by the user.

9. The apparatus of claim 8, wherein the processor is programmed to further determine that the clinical study and role are accessible by the user.

10. The apparatus of claim 9, wherein the data received from the user includes a second clinical task to be executed for the user.

11. The apparatus of claim 10, wherein the controller component is further operative to receive data operated on by the first registered clinical application.

12. The apparatus of claim 11, wherein the processor is programmed to:
further determine, using the controller component based on the second clinical task, a second registered clinical application associated with the second clinical task; and
execute the second clinical task using the second registered clinical application and the received data operated on by the first registered clinical application.

13. A computer-implemented method for providing a user access to clinical tasks, comprising:
registering, using a processor, a plurality of clinical applications associated with clinical tasks, each clinical application associated with at least one clinical task;
receiving, from the user, data identifying a first clinical task to be executed;
determining, using the processor, from the plurality of registered clinical applications, a first registered clinical application associated with the first clinical task;
further determining, using the processor, that the user is identified;
further determining, using the processor, that the first registered clinical application is accessible by the user; and
executing, using the processor, the first clinical task using the first registered clinical application.

14. The method of claim 13, further comprising receiving, from the user, data identifying a second clinical task to be executed.

15. The method of claim 14, further comprising receiving data operated on by the first registered clinical application.

16. The method of claim 15, further comprising:
determining a second registered clinical application associated with the second clinical task; and
executing the second clinical task using the second registered clinical application and the received data operated on by the first registered clinical application.

17. The method of claim 16, further comprising determining that the second registered clinical application is accessible by the user.

18. The method of claim 14, further comprising receiving, from the user, data regarding a clinical study and a role associated with the second clinical task to be executed.

19. The method of claim 18, further comprising determining, using the processor, a second registered clinical application associated with the second clinical task and with the clinical study and role.

20. The method of claim 19, further comprising determining that the second registered clinical application is accessible by the user.

* * * * *